United States Patent [19]

Martin et al.

[11] Patent Number: 5,322,787
[45] Date of Patent: Jun. 21, 1994

[54] CYTOKINE AND BIOASSAY THEREFOR

[75] Inventors: Michael Martin, West Brunswick, Australia; Jurgen Novotny, Ulm Donau, Fed. Rep. of Germany; Andrew Boyd, Ascot Vale, Australia; Nicos A. Nicola, Regent, Australia; Karen Welch, Vermont, Australia; William McKinstry, Northcote, Australia

[73] Assignee: Amrad Corporation Limited, Victoria

[21] Appl. No.: 876,480

[22] Filed: Apr. 30, 1992

[51] Int. Cl.⁵ .............................................. C12Q 1/02
[52] U.S. Cl. .................................. 435/240.2; 435/29; 435/240.1
[58] Field of Search ............... 435/29, 240.2, 240.21

[56] References Cited

U.S. PATENT DOCUMENTS

| 4,675,291 | 6/1987 | Yamamura et al. | 435/68 |
| 4,808,532 | 2/1989 | Stampfer | 435/29 X |
| 4,980,290 | 12/1990 | Reznikoff et al. | 435/240.2 |
| 5,093,259 | 3/1992 | Litlefield et al. | 435/240.2 |
| 5,130,144 | 7/1990 | Civin | 424/577 |
| 5,132,223 | 7/1992 | Levine et al. | 435/240.2 |

OTHER PUBLICATIONS

J. R. Novotny et al., Exp. Haematol. 18:755-784 (1990).
Brash et al., Strontium Phosphate Transfection of Human Cells in Primary Culture, Molecular and Cellular Biology, May 1987, pp. 2031-2034.
PCT Applicant's Guide, vol. 1, Annex M2.
Dictionary of Biochemistry and Molecular Biology, Second Edition, John Wiley & Sons, New York.

Primary Examiner—Douglas W. Robinson
Assistant Examiner—Harold Y. Pyon
Attorney, Agent, or Firm—Scully, Scott, Murphy & Presser

[57] ABSTRACT

The present invention contemplates a method for detecting a cytokine in a sample, said method comprising contacting an effective mount of said sample with an effective mount of SPGM-1 cells for a time and under appropriate conditions and then testing for the maintenance of said cells without loss of clonogenicity and tumorigenicity.

1 Claim, 14 Drawing Sheets

CYTOKINE AND BIOASSAY THEREFOR

FIELD OF THE INVENTION

The present invention relates generally to a bioassay for detecting cytokines capable of maintaining the clonogenicity and tumorigenicity of an Indicator cell line. The present invention also relates to a novel cytokine capable of modulating haemopoietic cells and cell events and capable of being detected by the bioassay.

BACKGROUND TO THE INVENTION

The cell line PGM-1 is a unique transplantable murine leukaemia generally maintained by serial passage in C3H/HeJ mice. The transient in vitro survival and proliferation of PGM-1 cells is absolutely dependent on stimulation of the cells by haemopoietic growth factors, and in particular, IL3 or GM-CSF. However, this in vitro survival and proliferation is always accompanied by differentiation of the cells to mature and non-dividing macrophages and granulocytes. These cells, once differentiated, neither form colonies in soft agar nor do they induce tumor formation in mice after sub-cutaneous injection and like normal differentiated myelomonocytic cells these die in 7 to 14 days. PGM-1 tumor cells, therefore, resemble granulocytic/monocytic progenitor cells in having the capacity to differentiate to mature cells upon appropriate stimulation. However, PGM-1 cells exhibit variability on serial passage through mice. To avoid the high biovariability of PGM-1 cells derived from freshly isolated tumors, a permanent cell line, SPGM-1, was established in a two step approach.

First, freshly isolated tumor cells were cultured in transwell inserts on cloned human stromal cells transfected with plasmid DNA encoding Simian virus 40 (SV40) early region (see J. R. Novotny et al., *Exp. Haematol.* 18; 755-784, 1990) allowing continuous exchange of soluble factors. After several days in transwell cultures, PGM-1 cells were removed and transferred to small tissue culture wells. These cells received fresh stromal cell conditioned medium (CM) every second day. After an initial lag phase, proliferation was observed and cells were subsequently cultured in normal tissue culture flasks. In order for the cells to maintain dependence on exogenous factors for growth, strict culture conditions, i.e. seeding at a defined density in the presence of 25% (v/v) of the cloned stromal cell line CM, were required. Passaging every second day under these conditions yielded a stable and permanent cell line which was designated SPGM-1 (deposited at Public Health Laboratory Service, European Collection of Animal Cell Cultures, Porton Down, Salisbury, UK, on 26 April, 1991 under accession number 91042620).

In work leading up to the present invention, the SPGM-1 cell line was used to establish a bioassay in order to identify and characterise factors released by cell lines such as the human stromal cell lines of Novotny et al., and/or recombinant synthetic or derivative forms of such factors.

SUMMARY OF THE INVENTION

Accordingly, a first aspect of the present invention contemplates a method for detecting a cytokine in a sample, said method comprising contacting an effective amount of said sample with an effective mount of SPGM-1 cells for a time and under appropriate conditions and then testing for the maintenance of said cells without loss of clonogenicity and tumorigenicity.

A second aspect of the present invention provides a biologically pure cytokine or synthetic or recombinant forms or derivatives thereof capable of maintaining undifferentiated SPGM-1 cells in vitro without loss of clonogenicity and tumorigenicity.

The following abbreviations are used in the subject specification:

| | |
|---|---|
| SV | Simian Virus |
| PGM | Pro Granulocyte - Macrophage |
| SPGM | Suspension PGM1 |
| HUVEC | Human Umbilical Vein Endothelial Cell |
| IL | Interleukin |
| CSF | Colony Stimulating Factor |
| SCF | Stem Cell Factor |
| S.C. | Sub cutaneous |
| HSCL | Human Stromal Cell Line |
| CM | Conditioned Medium |
| IMDM | Iscove's Modified Dulbecco's Medium |
| FCS | Fetal Calf Serum (Commonwealth Serum Laboratory) |
| SIGM | Surface Immunoglobulin M |
| FACS | Fluorescence activated cell sorter |
| r | Recombinant |
| M | Mouse |
| h | human |
| n | natural |
| HPLC | high performance liquid chromatography |

SPGM-1 cells were washed four times in culture medium without HSCl CM. 2000-16000 cells were seeded/well in 0.5 ml total volume in 24 well plates. Cells were cultured in the absence of HSCL CM (O-O) and in the presence of 25% (v/v) HSCL CM ( - ). After 7 days of incubation at 37° C., 10% $CO_2$, 90% air in a humidified atmosphere, aliquots of the cells we, removed and the number of cells counted using a hemocytometer.

Figure 1A:
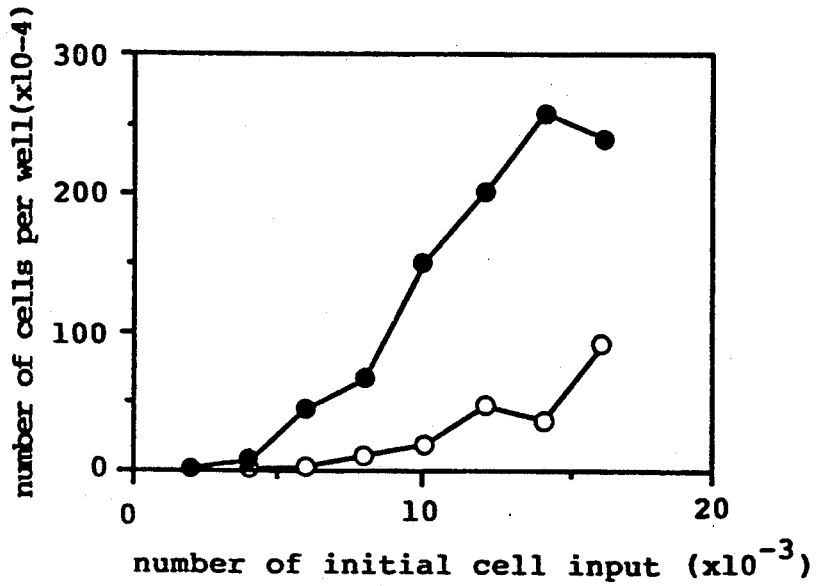
FIG. 1a is a graphical representation showing the proliferation of SPGM-1 cells in the absence and presence of HSCL CM.
Figure 1B:
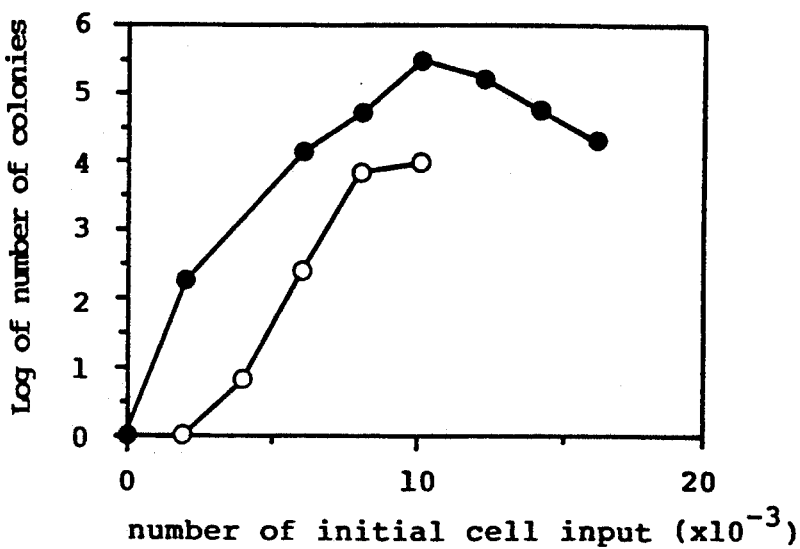

FIG. 1b is a graphical representation showing colony forming capability of SPGM-1 cells, cultured in suspension cultures for 7 days.

SPGM-1 cells had been cultured as described in FIG. 1a. The cells were removed on day 7 and conventional soft agar cultures set up using WEHI3B CM as source for the colony stimulating factor IL-3. After an incubation of 7 days (above conditions) the number of colonies were counted using a dissection microscope.

SPGM-1 had been cultured without (O-O) or with 25% (v/v) HSCL CM ( - ) in the first 7 days of the suspension culture of the 14 day assay.

Figure 2:
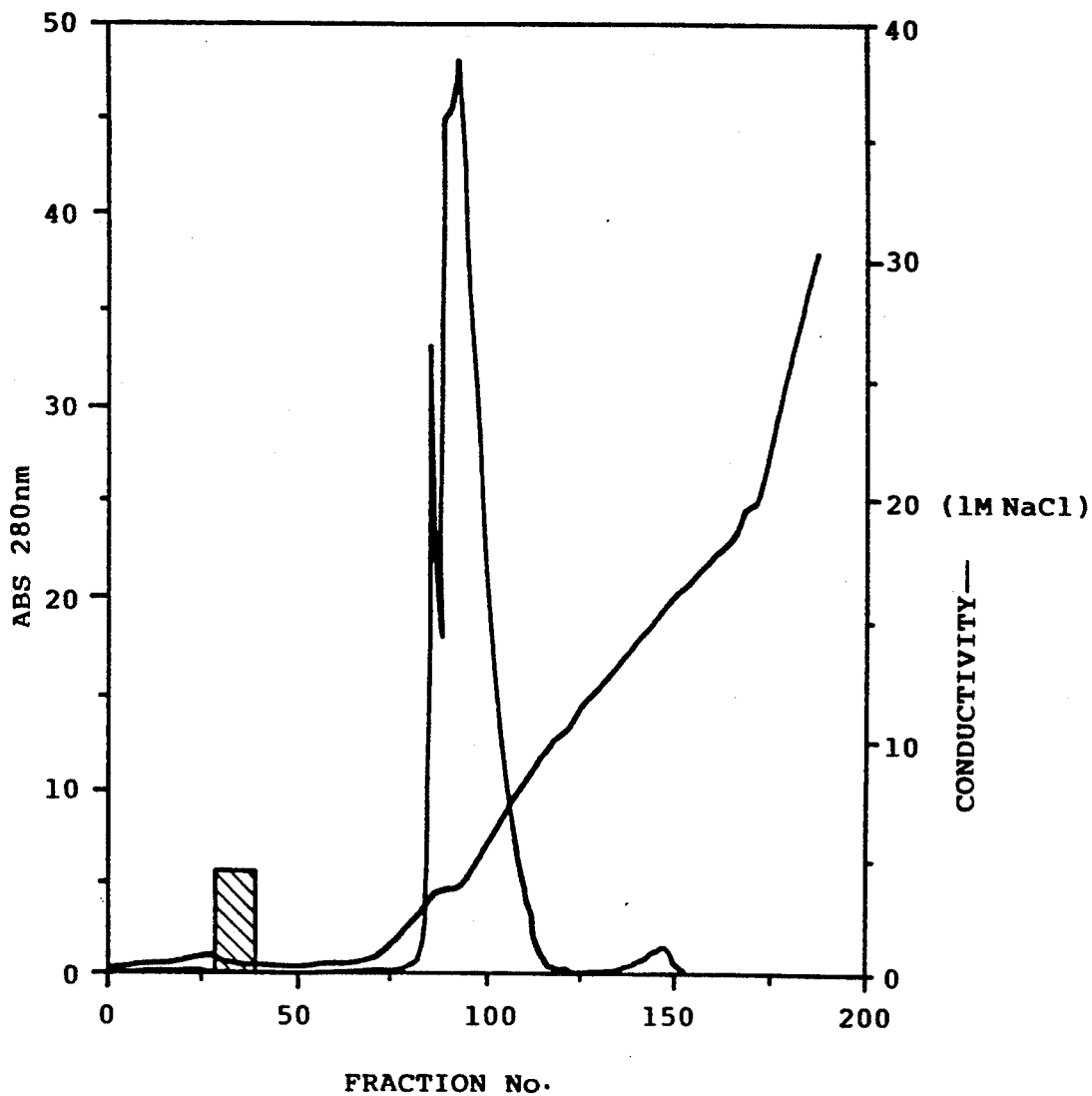

FIG. 2 is a graphical representation showing the absence of binding of the novel cytokine to DEAE-Sepharose CL-6B under conditions of low tonic strength and high pH. (10 mM Tris HCl, pH 8).

Figure 3:
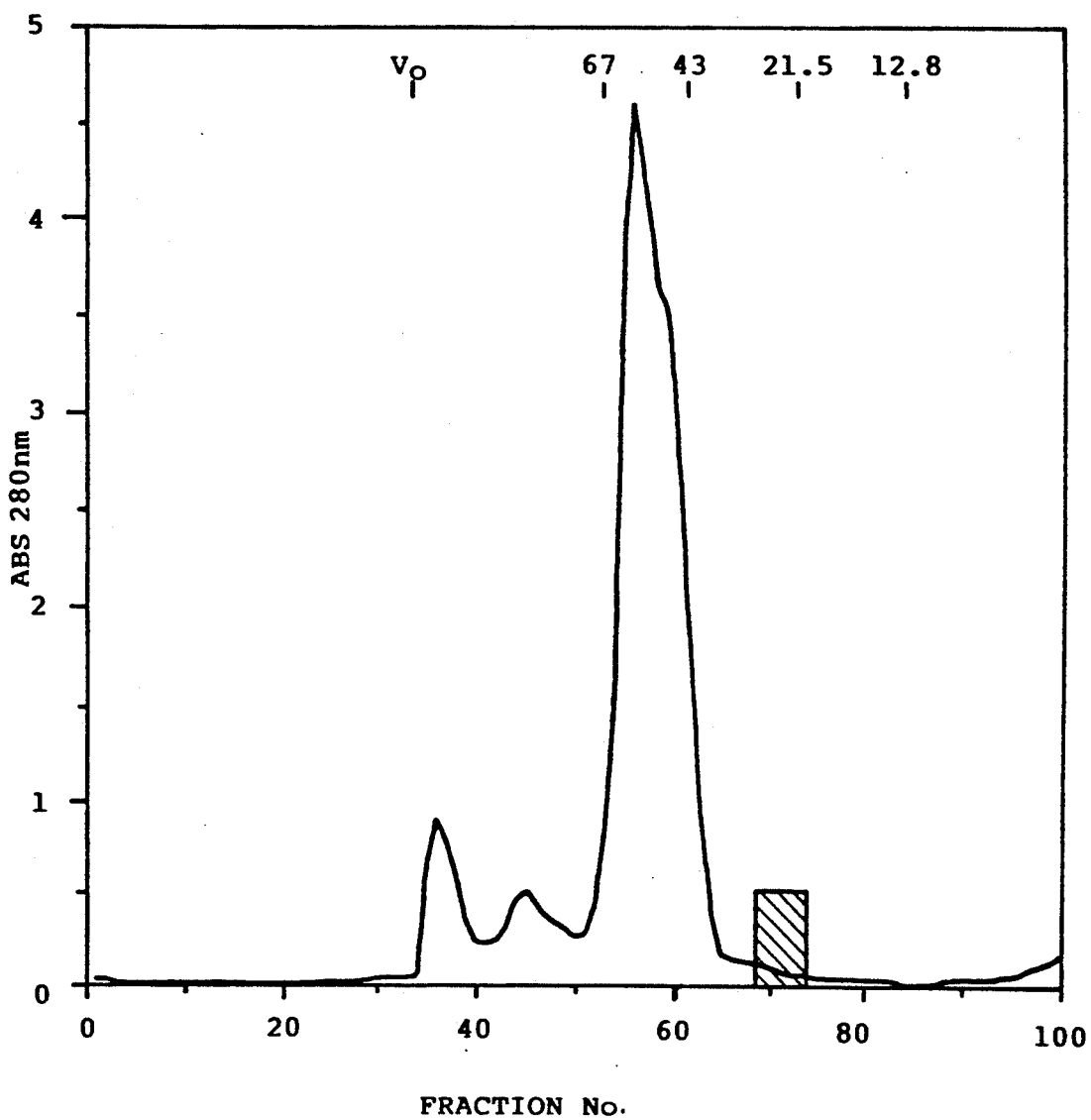

FIG. 3 is a graphical representation showing elution of the novel cytokine from a TSK-HW-55 gel filtration column (2.6×200 cm) in the 20-25 kDa region. Elution was with 10 mM sodium phosphate buffered (pH 7.4 ) saline (0.15M) at 15 ml/hr.

Figure 4:
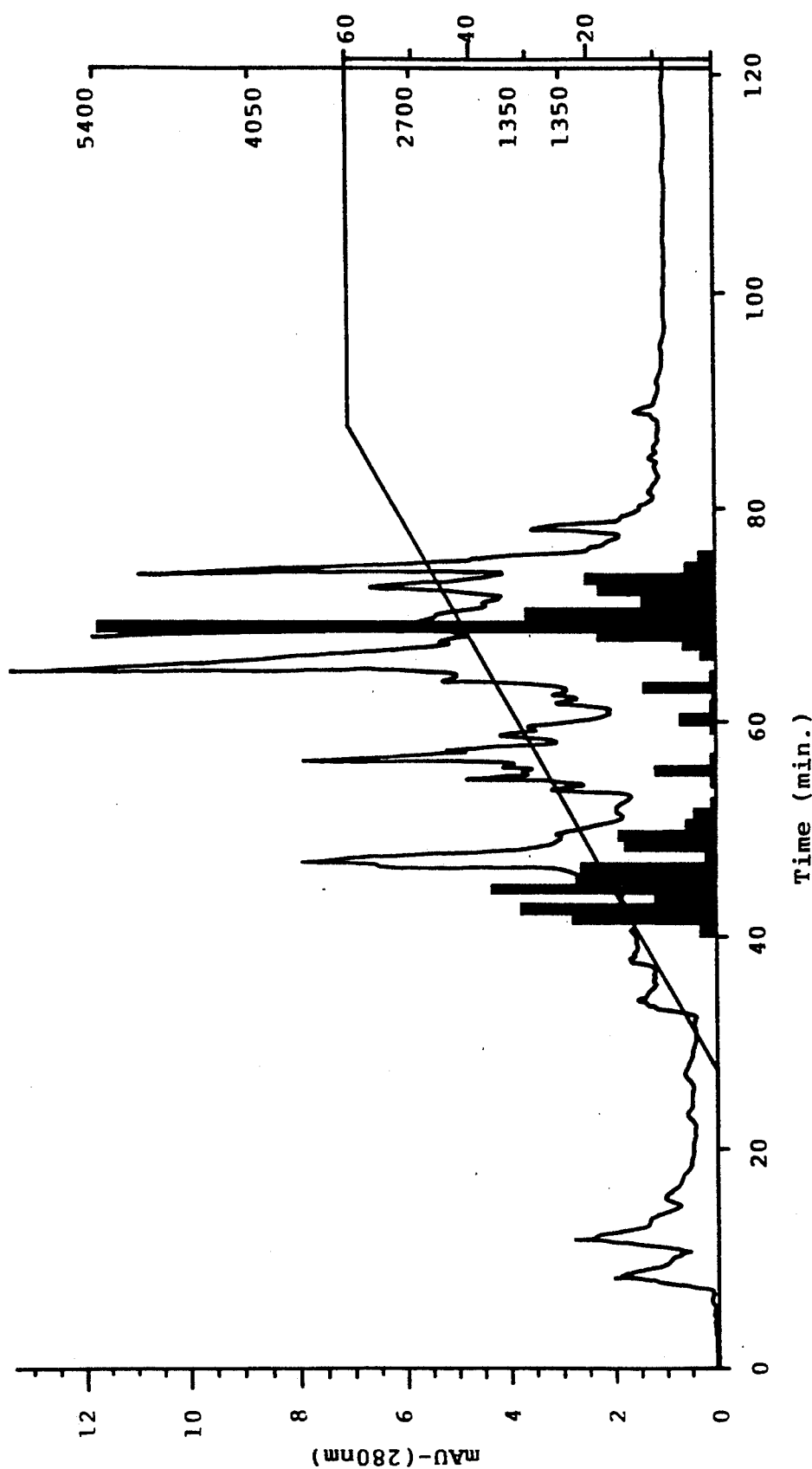

FIG. 4 is a graphical representaion showing elution of the novel cytokine from a reverse phase HPLC column (Aquapore RP 300 C8,7×250 mm) using a 0-60% (v/v) acetonitrile gradient in water containing 0.1% (v/v) trifluoroacetic acid at 1 ml/min.

Figure 5A:
Figure 5B:
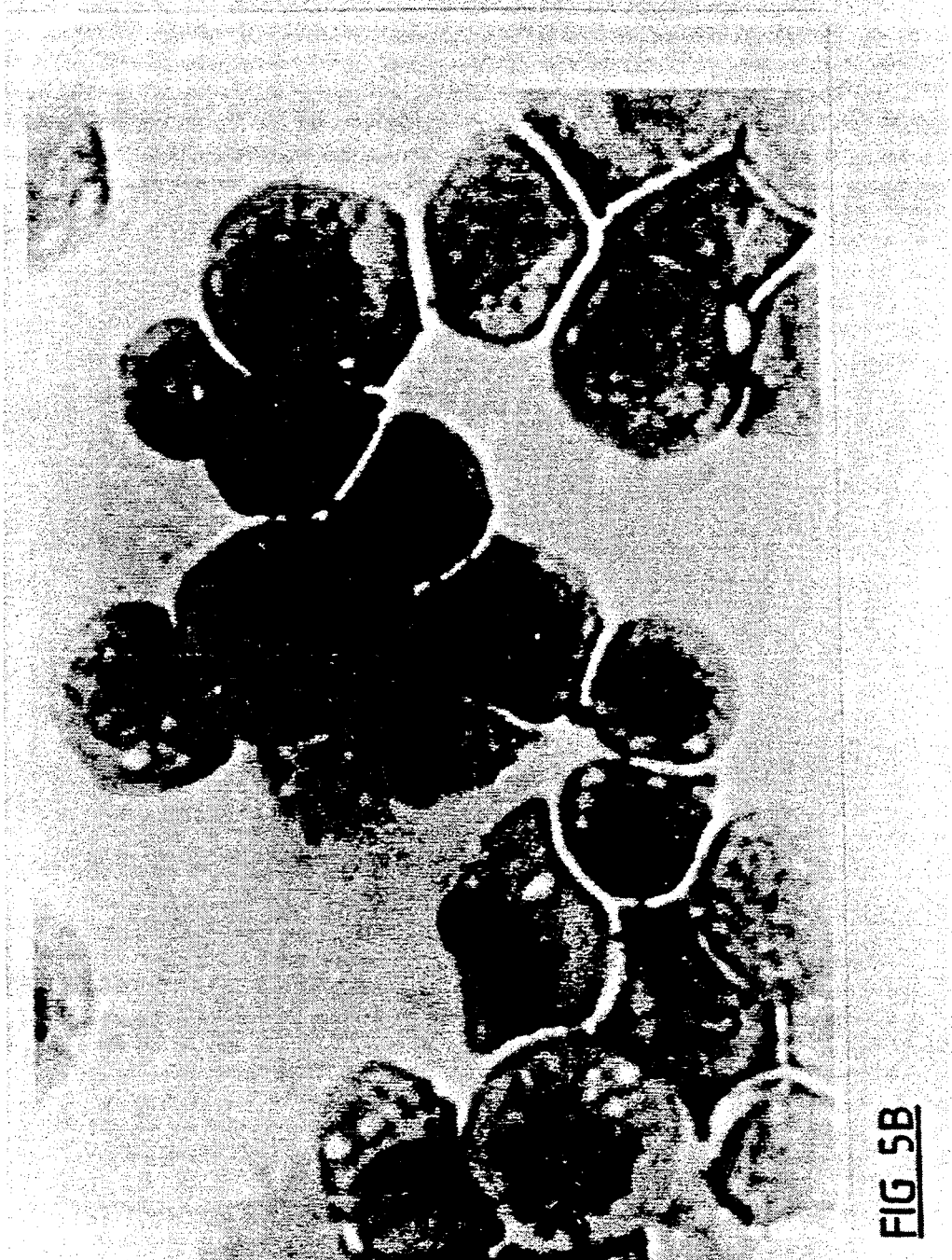

FIG. 5 is a photographic representation showing FIG. 5a) SPGM-1 cells in suspension culture in the presence of HSCL CM (undifferentiated). FIG. 5b) SPGM-1 cells in suspension culture after differentiation with 1000U/ml IL-3.

Figure 6A:
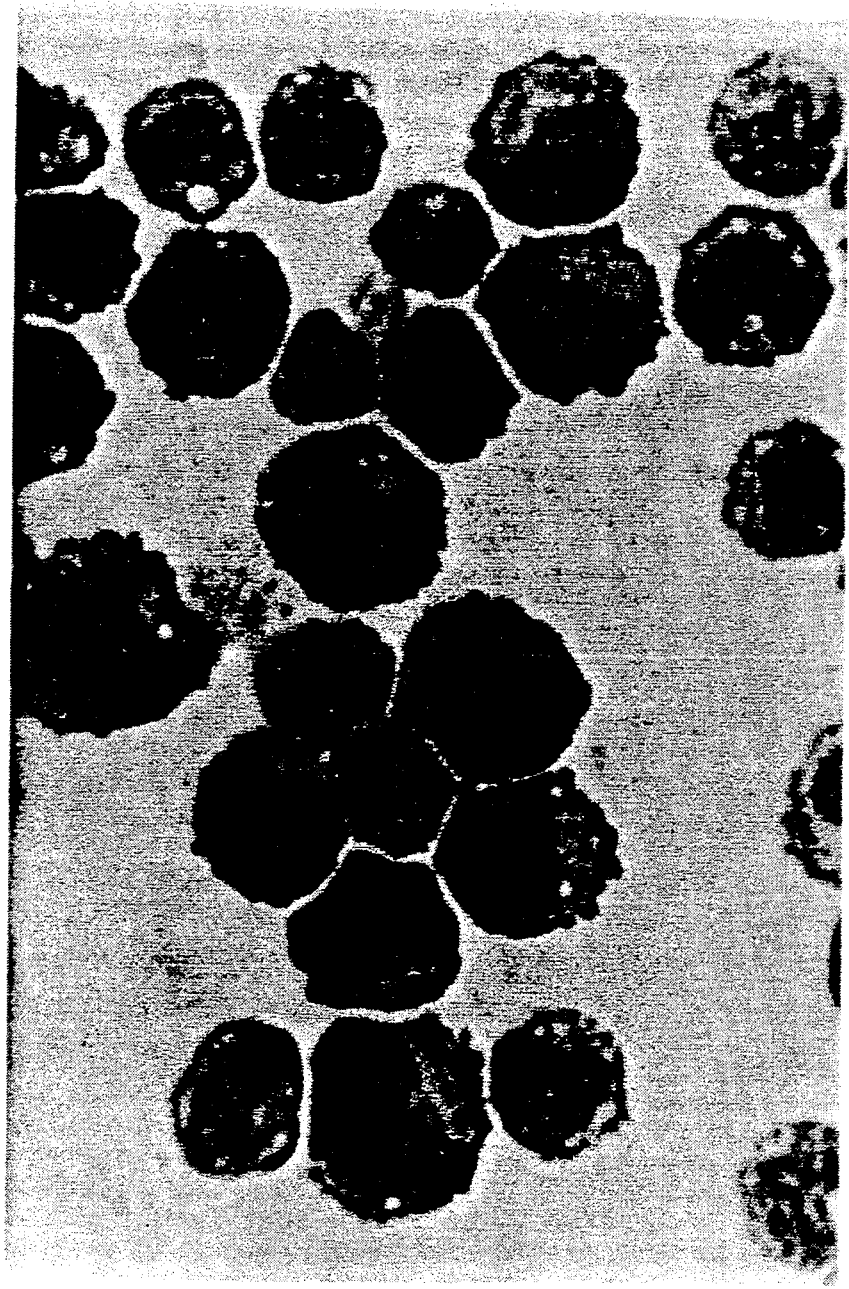
Figure 6B:
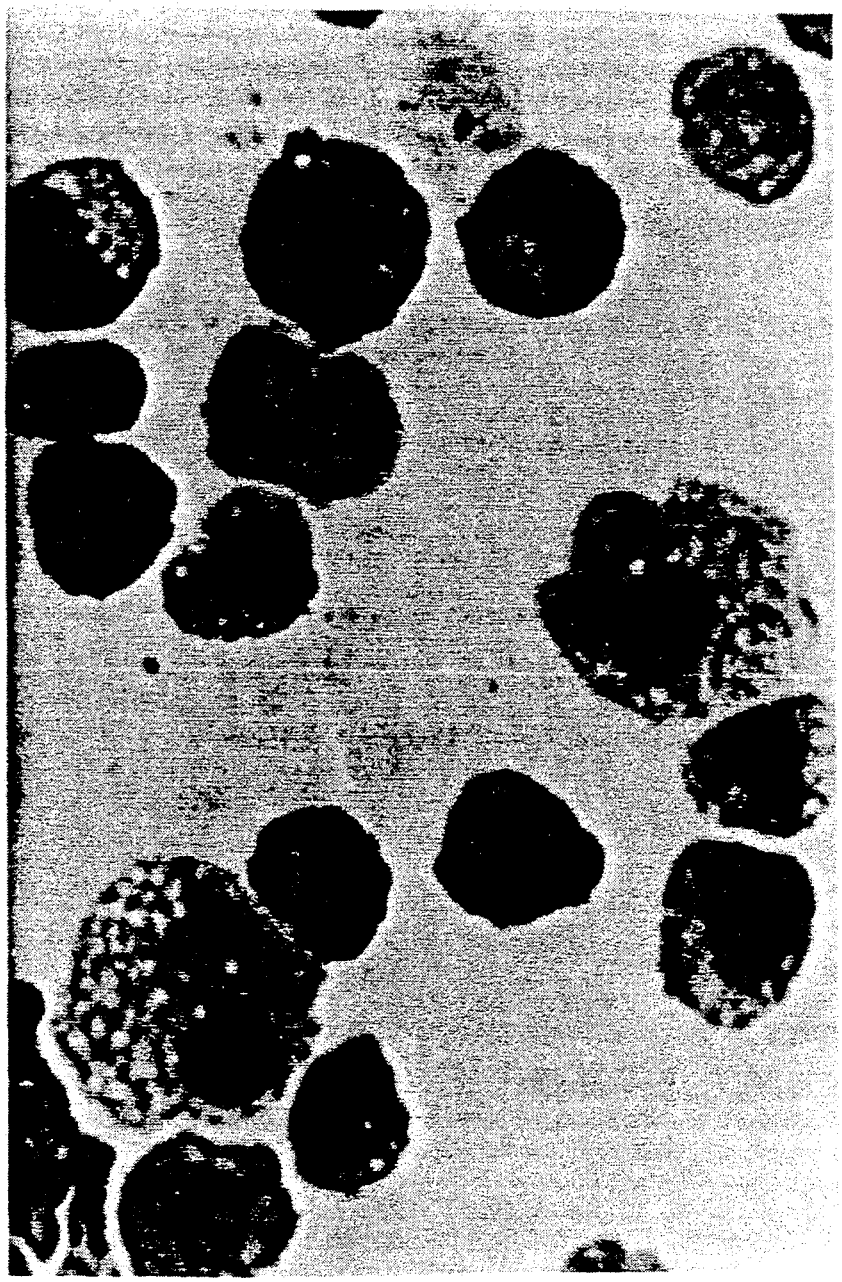

FIG. 6 is a photographic respresentation showing FIG. 6a) Cytospins of SPGM-1 cells in suspension culture (undifferentiated=blast cells). FIG. 6b) Cytospins of SPGM-1 cells in suspension culture in the presence of 20% WEHI3B CM for 7 days (differentiated=-monocytic/macrophages).

Figure 7:
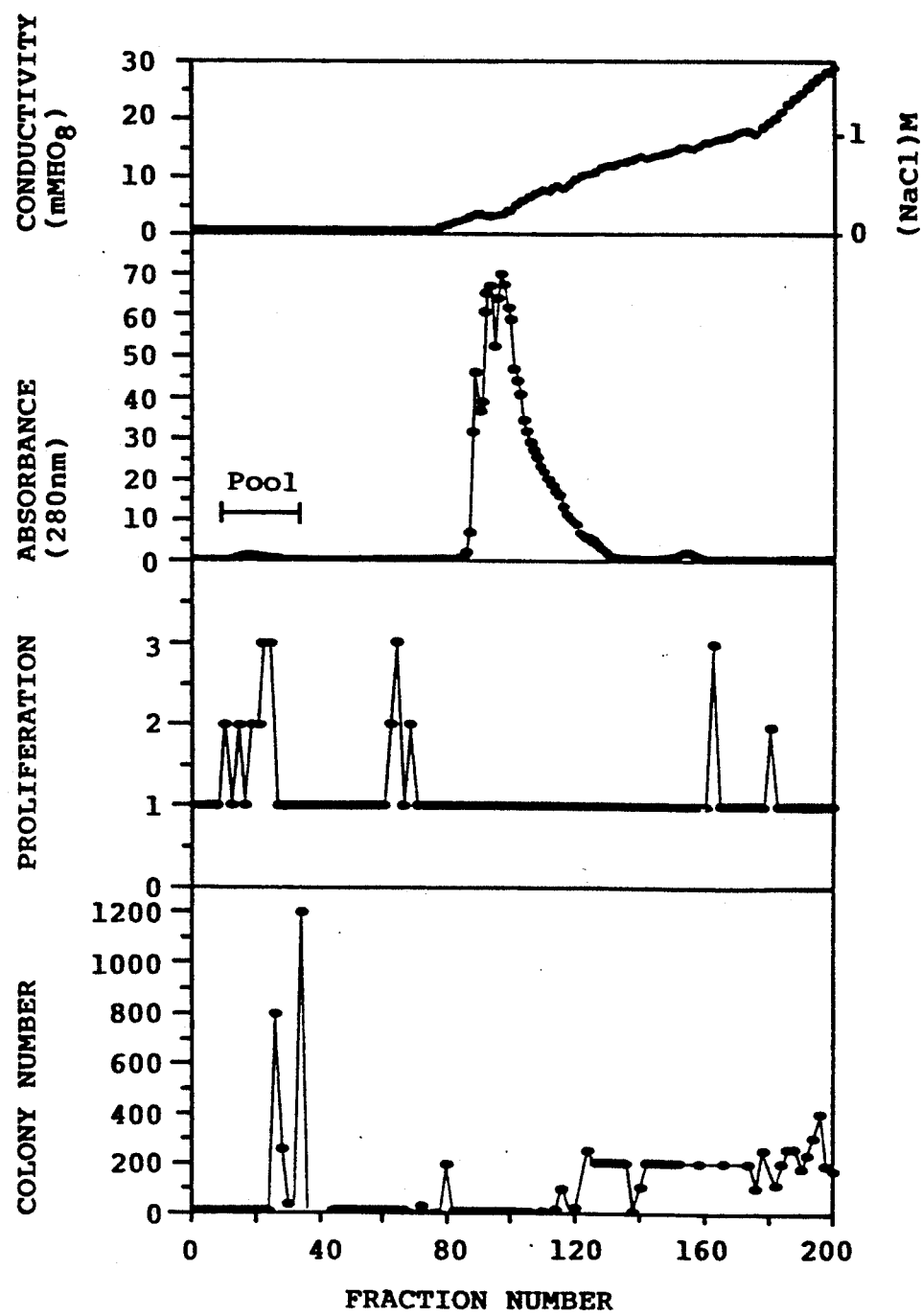

FIG. 7 is a graphical representation showing anion exchange chromatography of concentrated HSCL 197/17CM. Concentrated HSCL 197/17 CM was applied to a column of DEAE-sepharose CL-6B equilibrated in 10mM TRIS-HCl pH 8.0/0.01% Tween-20 (v/v)/0.02% sodium azide (w/v). The column was eluted isocratically and then developed with a linear gradient of 0–2M NaCl in equilibration buffer. From the top-most panel are shown, the concentration of NaCl in elutant as determined by conductivity, followed by the absorbance of fractions at 280 nm, and the capacity of fractions diluted 1:50 to stimulate proliferation of SPGM-1 cells in a seven day suspension culture assay, and the subsequent ability of these cells to form colonies in soft agar in the presence of WEHI3B D- CM/endothelial cell CM.

Figure 8:
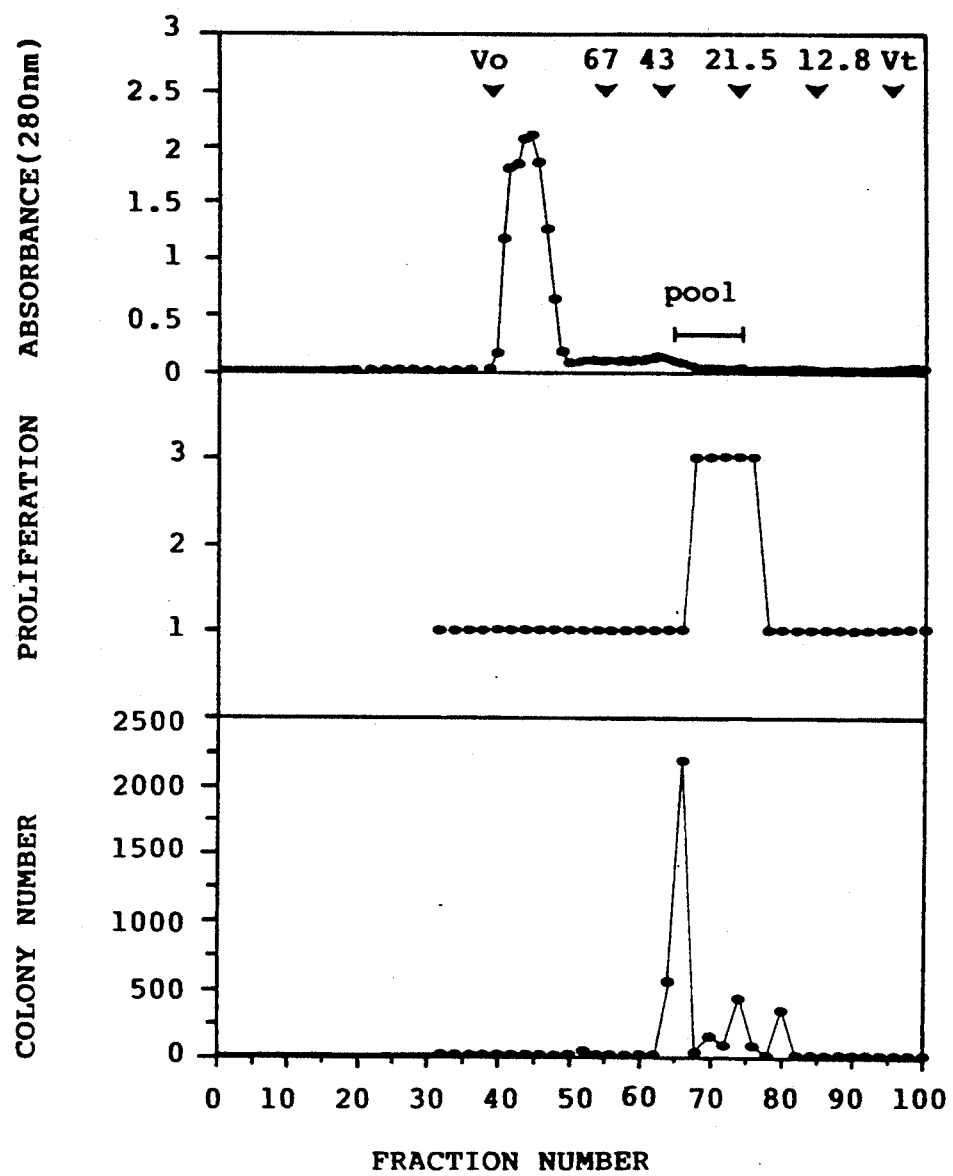

FIG. 8 is a graphical representation of gel filtration chromatography of PGM-1 activity that eluted from DEAE-sepharose CL-6B. Fractions that eluted in the breakthrough of DEAE-sepharose CL-6B containing PGM-1 activity were pooled, concentrated and applied to a column of Ultrogel ACA 44 equilibrated in mouse tonicity phosphate buffered saline pH 7.2/0.02% isocratically. From the top-most panel are shown, the absorbance of fractions at 280 nm, and the capacity of fractions diluted 1:100 to simulate proliferation of SPGM-1 cells in a seven day suspension culture assay, and the subsequent ability of these cells to form colonies in soft agar in the presence of WEHI 3B D-CM/endothelial cell CM. The fraction number is shown on the abscissa, and the elution positions from left to right of bovine serum albumin (67 KDa), ovalbumin (43 KDa), soya bean trypsin inhibitor (21.5 KDa), and cytochrome C (12.8 KDa) are denoted by arrows above the upper panel. The void and total volumes were determined using blue dextran and vitamin B12 respectively.

Figure 9:
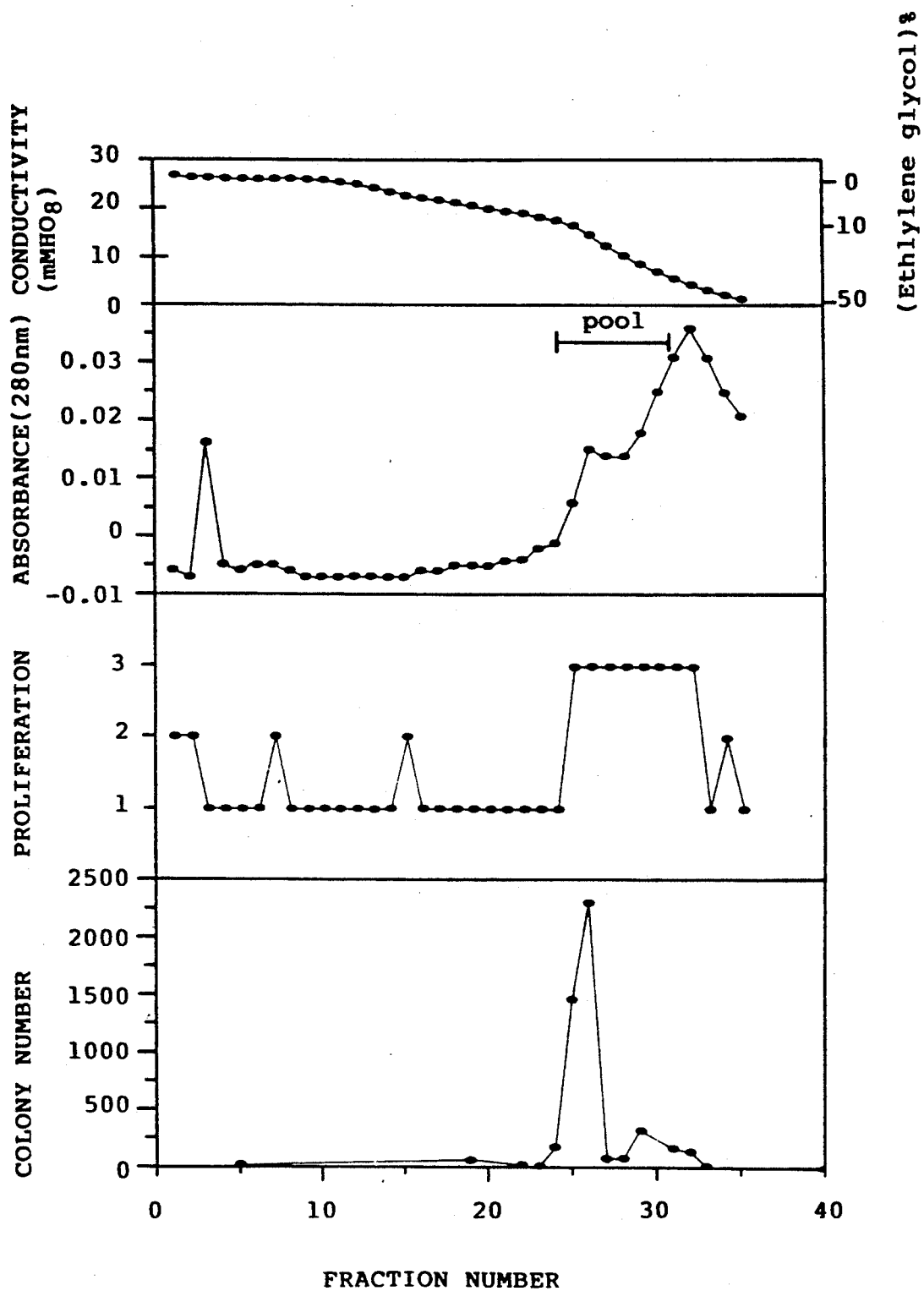

FIG. 9 is a graphical representation depicting hydrophobic interaction chromatography of PGM-1 activity that eluted from ACA44. Fractions that eluted from ACA 44 between 40KDa and 20KDa and contained PGM-1 activity were pooled, concentrated and exchanged into 100 mM sodium phosphate buffer pH 7.0/1.0M sodium sulphate/0.02 (v/v) Tween-20 (v/v)/0.02 (w/v) sodium azide and applied to a column of phenyl-sepharose CL-4B equilibrated in the same buffer. The column was eluted isocratically followed by successive linear gradients of 0–10% ethylene glycol and 10–50% (w/v) ethylene glycol in 100mM sodium phosphate buffer pH 7.0. From the top-most panel are shown, the concentration of ethylene glycol in elutant as determined by conductivity, followed by the absorbance of fractions at 280 nm, and the capacity of fractions diluted 1:50 to stimulate proliferation of SPGM-1 cells in a seven day suspension culture assay, and the subsequent ability of these cells to form colonies in soft agar in the presence of WEHI3B D- CM/endothelial cell CM.

Figure 10:
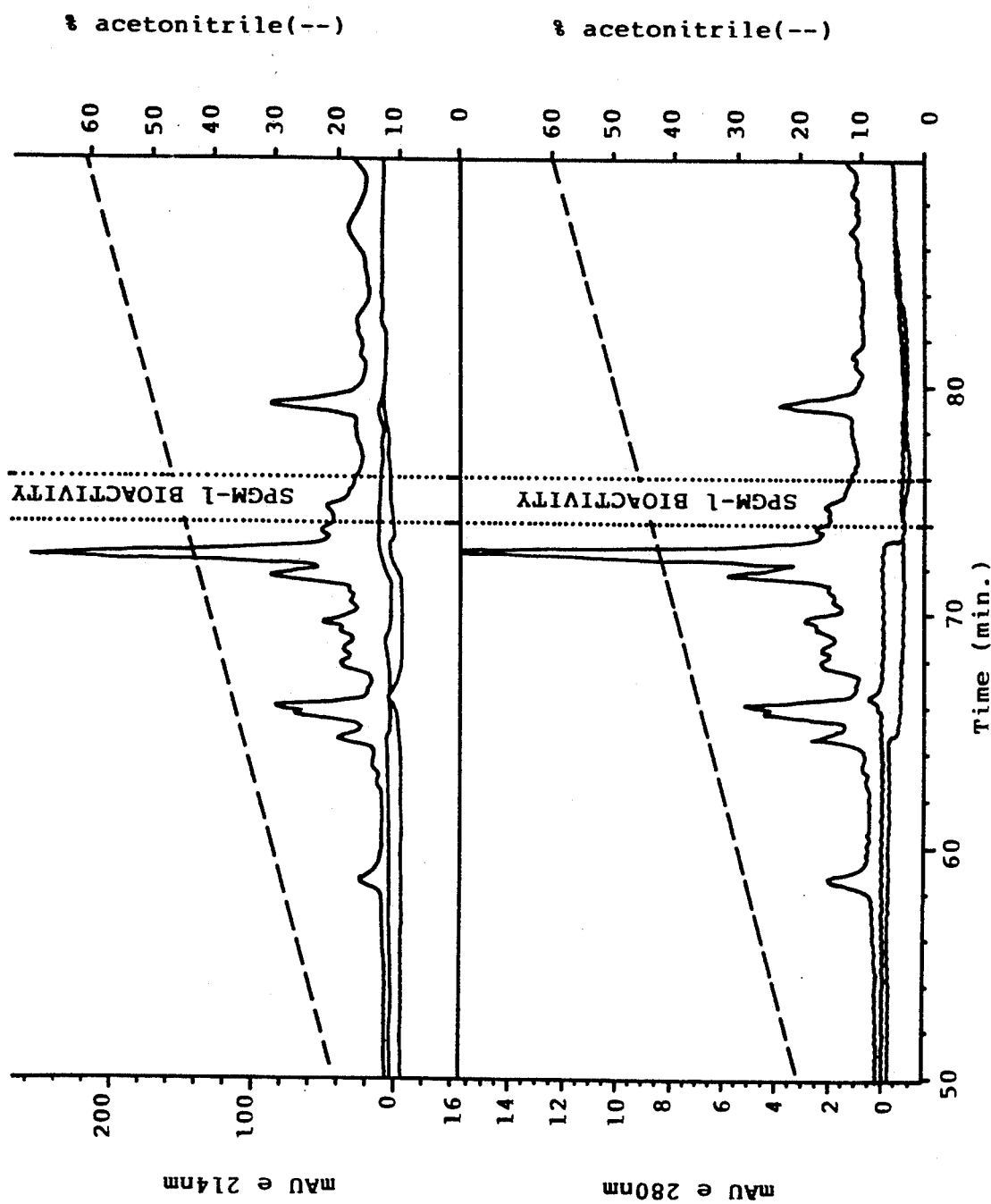

FIG. 10 is a graphical representation showing RP HPLC of the PGM-1 activity that bound to phenyl-sepharose CL-4B. Fractions that bound to phenyl-sepharose CL-4B and containined PGM-1 activity were pooled, concentrated, exchanged into mouse tonicity phosphate buffered saline pH7.2/0.02% Tween-20 (v/v)/0.02% (w/v) sodium azide, and applied to a Aquapore RP300 C8 HPLC column with a mobile phase of water containing 0.1% TFA. The column was eluted isocratically (20 ml) and then a 60 minute gradient from 0–60% (v/v) acetonitrile containing 0.085% TFA applied. From the uppermost panel are shown concentration of acetonitrile % (v/v), absorbance of fractions at 214 nm and 280 nm, and the capacity of the fractions to stimulate proliferation of SPGM-1 cells in a seven day suspension culture assay.

Figure 11:
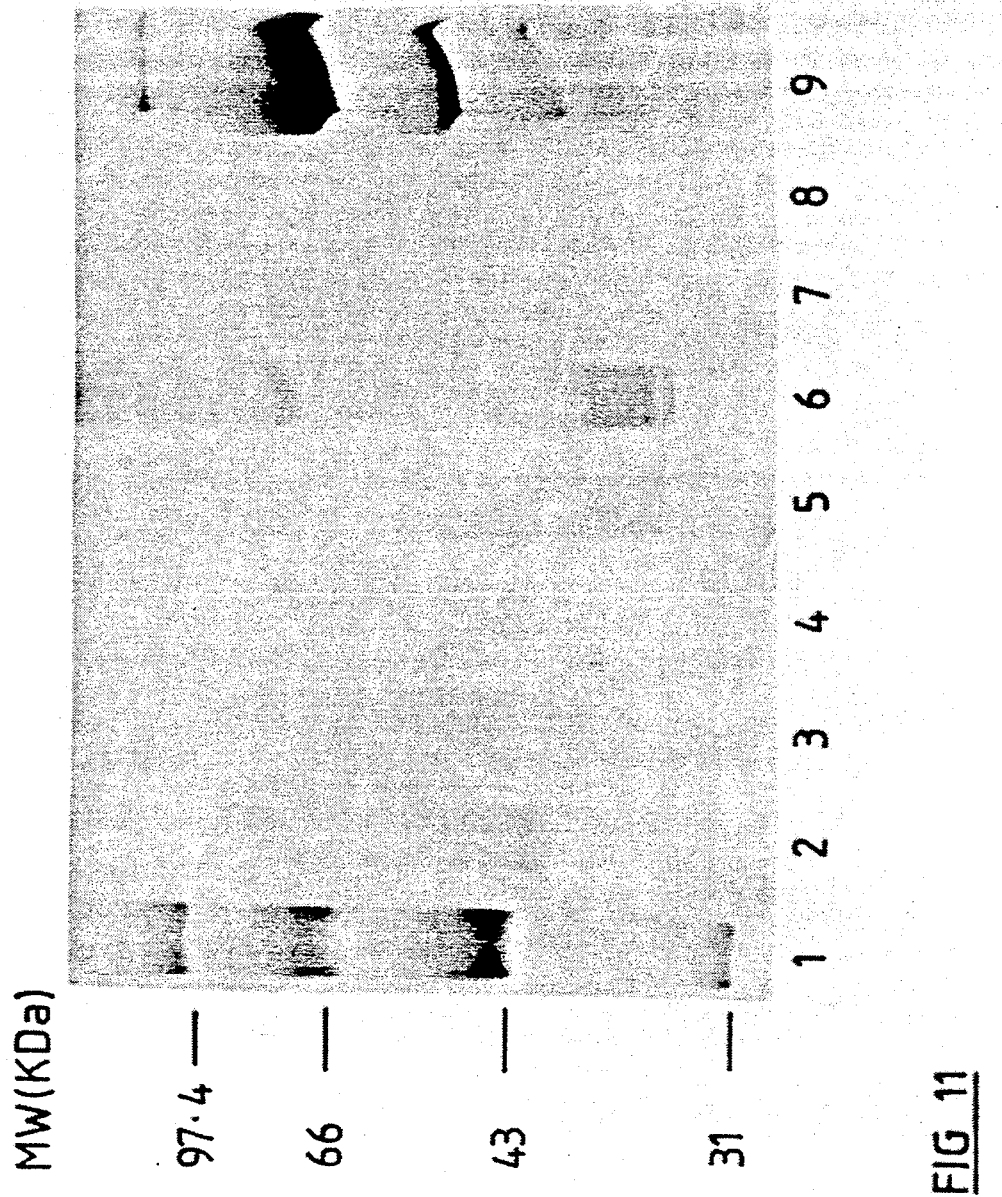

FIG. 11 is a photographic representation of an SDS-PAGE gel showing molecular weight bands purified from HSCL 197/17 CM.

Figure 12:
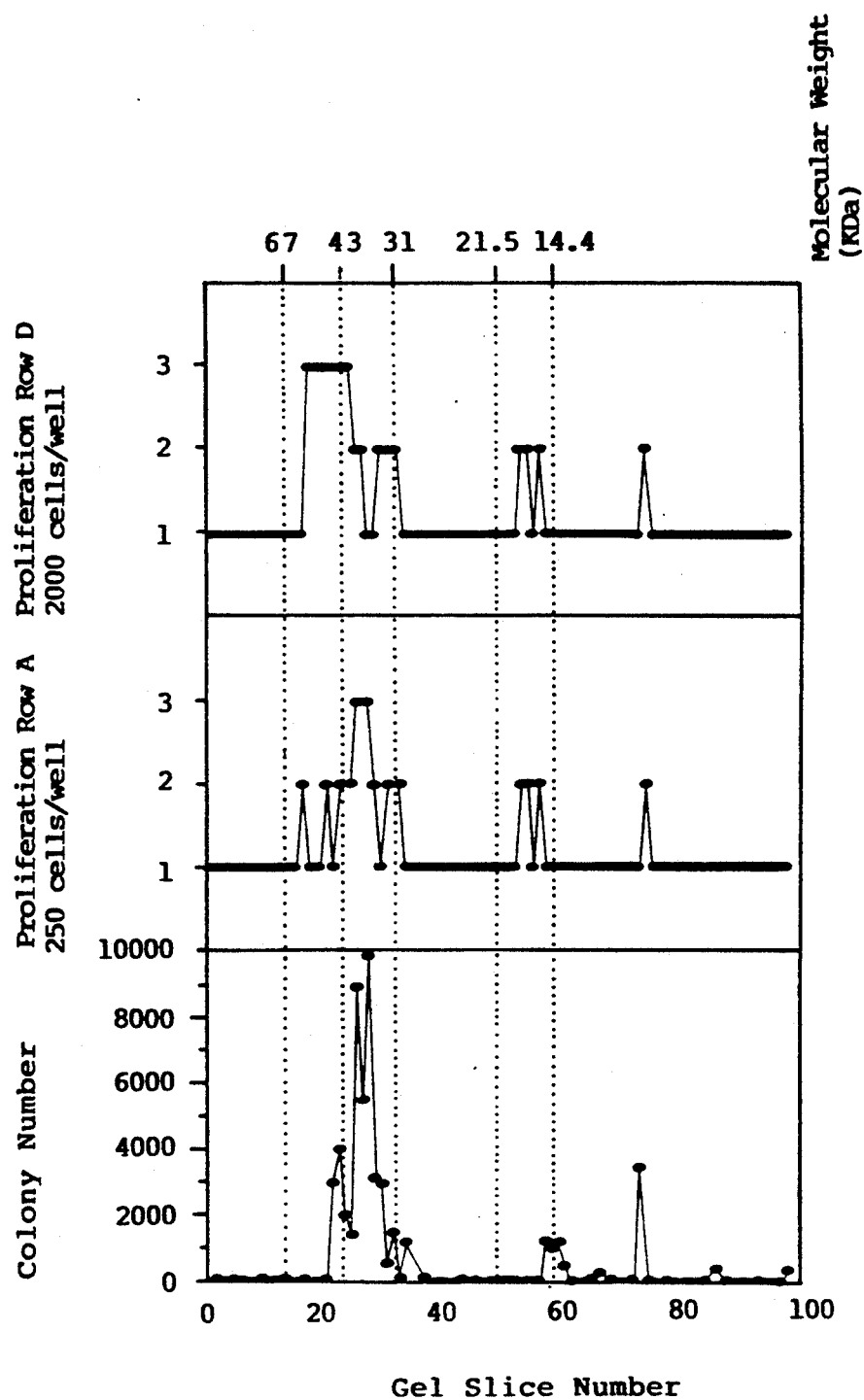

FIG. 12 is a graphical representation of SDS-PAGE of semi-purified PGM-1HSCl 197/17 CM. PGM-1 activity semi-purified from HSCL 197/17 CM using anion exchange, gel filtration and RP-HPLC chromatography was electrophoresed on a 15% (w/v) polyacrylamide gel, in the presence of SDS under non-reducing conditions. The gel was sliced up into 1 mm slices, homogenised in 6M guanidine-HCl containing 1 mg/ml bovine serum albumin (carrier protein). From the top-most panel are shown the position of molecular weight markers,.and the capacity of fractions diluted 1:500 to stimulate proliferation of SPGM-1 cells (seeded at an initial density of 2000 and 250 cells/well) in a seven day suspension culture assay, and the subsequent ability of these cells to form colonies in soft agar in the presence of WEHI 3B CM/endothelial cell CM.

DETAILED DESCRIPTION OF THE INVENTION

According to a first aspect of the present invention, there is provided a method or bioassay for the detection of a cytokine in a sample capable of the in vitro maintenance of undifferentiated SPGM-1 cells without loss of clonogenicity and tumorigenicity. In a preferred embodiment, the cytokine is of mammalian cell origin and preferably human cell origin. Most preferably, the cytokine is of human stromal cell origin. The bioassay is preferably conducted as follows. An effective amount of SPGM-1 cells in Iscove's Modified Dulbecco's Medium (IMDM) and 10% v/v fetal calf serum (FCS) are mixed with an effective mount of sample such as CM from a cloned human stromal cell line and the cells seeded in a tissue culture flask. The effective amounts will vary depending on the sample to be tested and the respective concentrations of SPGM-1 cells and cytokine to be detected. One skilled in the art would readily determine the optimum mounts by routine experimentation. Generally, the effective amount is from about $10^2$ to about $10^{10}$ cells, preferably from about $10^4$ to about $10^8$ cells and most preferably from about $10^5$ to about $10^7$ cells. The cells are then cultured at 37° C. in a fully humidified incubator in 10% v/v $CO_2$ in air for about one to fifteen days, preferably one to about ten days and most preferably from two to five days and the cell number and viability then assessed. The maintenance of clonogenicity of the cells after this time but generally after about seven to ten days in suspension culture is then tested using, for example, conventional soft agar cultures set up in the presence of murine WEHI 3B CM as a source of IL-3 as a differentiating agent. After a suitable incubation time, for example seven days, in a fully humidified atmosphere of 10% v/v $CO_2$ in air at 37° C., colonies are counted using a dissection microscope. One skilled in the art will immediately recognise that the assay conditions, the media and the sample (e.g. CM) employed may be varied to suit the conditions, the laboratory and the expertise or otherwise of the technician or experimenter. All such variations are encompassed by the present invention.

The term "sample" is used in its broadest and most general sense to encompass all naturally occurring and artifical sources such as, but not limited to, biological samples of the type including bood, plasma and serum and other body fluids such as lymph, excreta, nasal and respiratory fluid as well as tissue, tissue extracts and tissue fluid. The sample may also be culture medium, conditioned medium, fermentation medium whether or not the medium has undergone a partial or full purification process such as into fractions. The sample may also be a fraction from a chromatography column or from an electrophoresis gel. Additionally, the sample may be a recombinant product or a reconstituted naturally occurring or recombinant product.

The bioassay is particularly useful in detecting factors acting on early myeloid progenitors and, hence, for factors potentially useful as haemopoietic cell regulators. The assay can be conducted using relatively crude or semi-purified samples such as condition medium or a fraction thereof or using purified known or unknown factors.

The bioassay may conveniently be provided in kit form. According to this aspect of the present invention, there is provided a kit for detecting a cytokine in a sample comprising in a compartment form a first compartment adapted to contain SPGM-1 cells and optionally additional compartments adapted to contain reagents for use in the method, such as IMDM, FCS, buffers and diluents. Preferably, the SPGM-1 cells are in cryopreserved form in the kit. Preferably, the SPGM-1 cells are cryopreserved at approximately $10^6$–$10^7$ cells/ml and this may conveniently be packed in one or more vials containing from 0.1 to 100 ml, and preferably 1 to 50 ml.

Another aspect of the present invention provides a novel cytokine of, in a preferred embodiment, stromal cell origin, and, preferably mammalian stromal cell origin and in particular, human stromal cell origin. The novel cytokine is conveniently detected using the SPGM-1 bioassay as hereinbefore described. The cytokine does not bind to DEAE-Sepharose CL-6B under low ionic strength (e.g. 20 mM buffer) pH 8 suggestive of an isoelectric point (pI) greater than 8. The molecular weight of the naturally occurring cytokine is approximately 30–50 kDa and more specifically 30 to 45 kDa and even more specifically 33 to 43 kDa. The present invention extends to a cytokine with a molecular weight outside this range due to, for example, variations in expression of the naturally occurring cytokine or its recombinant or synthetic equivalents or any derivatives thereof resulting in altered glycosylation patterns and/or the natural or artifical addition, deletion and/or substitution of amino acids to the sequence. The cytokine is conveniently isolated from CM of Human Stromal Cell Line 197/17 (deposited at Public Health Laboroatory Service, European Collection of Animal Cell Cultures, Porton Down, Salisbury, UK on 19 Apr., 1991 under provisional accession no. 91041959) and has utility in modulating haemopoietic cells and cell events.

Preferably, the novel cytokine is biologically pure, existing as the major or sole activity in a sample. Alternatively, the cytokine is part of a CM or a fraction thereof. The cytokine is biologically distinct from IL-1 α, IL-3, IL4, IL-7, G-CSF, GM-CSF, M-CSF, IL-6 and SCF. Although the present invention is described in terms of the cytokine in naturally occurring form, It clearly extends to recombinant or synthetic forms of the molecule, to glycosylated and unglycosylated forms thereof and any mutants, derivatives and/or homologues thereof whether or not such forms are biologically pure. The latter include single or multiple amino acid deletions, substitutions and/or additions to the naturally occurring or recombinant or synthetic molecule or any single or multiple deletions, substitutions and/or additions of molecules associated with the novel cytokine such as carbohydrates, lipids and proteins. The present invention also extends to the novel cytokine existing, in part or totally, as a fusion molecule to a polypeptide or protein such as, but not limited to, another cytokine or β-galactosidase or glutathione-S-transferase. The term "biologically pure" includes preparations comprising at least 30% preferably at least 50%, more preferably at least 70% and still more preferably at least 90% of the cytokine relative to other proteins as determined by weight and/or activity. In a most preferred embodiment, the cytokine is purified according to the procedure described in Example 4.

Although the present invention is described using the isolation of the novel cytokine from a human stromal cell line, and in particular, cell line 197/17, the method is equally applicable to the isolation of similar cytokines from non-human cell lines or even human non-stromal cell lines and the present invention extends to such factors.

Furthermore, the subject invention extends to compositions and in particular a pharmaceutical composition comprising the novel cytokine described herein. Additionally, the bioassay of the present invention provides a convenient screening procedure to identify agonists and/or antagonists of the novel cytokine and such agonists and antagonists are within the scope of the present invention.

The present invention is further described by the followinng non-limiting Examples.

EXAMPLE 1

Bioassay

The present example describes the bioassay using CM as the sample. This in no way limits the scope of the present invention which extends to all samples as hereinbefore defined.

A vial of SPGM-1 tumor cells stored under liquid nitrogen in 10% w/v DMSO/20% v/v FCS in IMDM is rapidly thawed (generally at 37° C.), the cells transferred to a 10 ml test tube, and 10 times the volume of culture medium added to resuspend the cells. The cells are centrifuged (1200 rpm, 8 min, 4° C.), the medium carefully removed and the pellet resuspended in 3.75 ml IMDM+10% (v/v) FCS 445. An aliquot of 1.25 ml fresh human stromal cell line (HSCL) conditioned medium (CM) is added and cells seeded in 5 ml total volume in a 25 $cm^2$ tissue culture flask (Nunc). Cells are cultured at 37° C., 10% (v/v) $CO_2$, 90% (v/v) air for 3 days, and the cell number and viability are then assessed (Trypan blue exclusion, 0.05% (v/v) final conc.). For further culture, $1 \times 10^6$ viable SPGM-1 cells are seeded under the above conditions for a 48 hour culture period then cells are counted and seeded at approximately $2 \times 10^6$ cells/5 ml in 25 cm² flasks for 24 hours. In order to use only actively proliferating cells in the bioassay, SPGM-1 cells are seeded at $1 \times 10^6$ cells/ml 24 hours prior to use. Commonly they double in number during the 24 hour period and have a viability ranging from 85-95%. On the day of the assay, SPGM-1 cells are washed 4 times by centrifugation and resuspension in IMDM+10% (v/v) FCS 445 without CM in order to remove remaining factor from the cells.

The washed cells are counted and adjusted to a final concentration of 5000 cells/ml in IMDM+10% (v/v) FCS 445. To compensate for cell density effects, four different cell concentrations are generally used: approximately 250; 500; 1000 and 2000 cells/well in a total volume of 0.5 ml/well. Serial dilutions of samples to be tested for bioactivity are used at about 100 μl/well (20% v/v). Cells are always added last. Since 24 well plates show interplate variability, a negative control (i.e. medium alone) and a positive control are added to each plate. Plates are incubated at 10% (v/v) $CO_2$, 90% (v/v) air in a fully humidified incubator at 37° C. for 7 days. After that period, cell viability and numbers are scored using a phase contrast microscope.

Criteria used for the identification of the novel cytokine activity in the bioassay include:

cell survival (number of viable cells)

(b) cell proliferation (total number of cells)

The second step of the bioassay tests for the maintenance of clonogenicity of the cells after 7 days in suspension culture. For this purpose, conventional soft agar cultures are set up in the presence of murine WEHI 3B CM containing IL-3 as a differentiating agent. After an additional 7 days of incubation at 10% (v/v) $CO_2$ 90% (v/v) air, 37° C. in a humidified atmosphere, colonies are counted using a dissection microscope.

EXAMPLE 2

Production of the Novel Cytokine From Human Stromal Cell Line 197/71

The SV40 large T transfected human bone marrow stromal cell line HSCL 197/17 (Novotny at al., supra) is expanded and a large number of cells are cryopreserved. From this stock, cells are used for expansion from 80 cm² tissue culture flasks to 175 cm² roller bottles. In the roller bottles, cells are grown initially in the presence of 5% (v/v) FCS 445. After the first 72 hours, medium is completely changed and FCS content reduced to 2% final concentration. Media are changed after 48 hours or 72 hours and collected.

Fresh media are immediately concentrated 10-20 times. Aliquots are tested in the bioassay for content of the bioactivity and stored frozen.

SPGM-1 is a unique murine tumor cell line which proliferates in vitro in the presence of conditioned medium of the human stromal cell line HSCL 197/17. At high cell concentrations, the cell line becomes independent of the stromal cell conditioned medium (FIG. 1A). Under these conditions, the cells proliferate and maintain their ability to form colonies in soft agar in the presence of differentiating cytokines, e.g. mIL-3. The number of colonies in soft agar correlates directly to the number of cells after one week of suspension culture in the presence of HSCL CM or cultured at high cell densities (FIG. 1B). Other cytokines are able to maintain viability of SPGM-1 cells cultured at low cell densities in vitro but they induce terminal differentiation accompanied by the loss of clonogenicity and tumorigenicity e.g. mIL-3.

The phenotype of SPGM-1 cells remained unchanged over a prolonged period of in vitro cultivation in the presence of stromal cell CM. The panel of antibodies used to establish the phenotype of SPGM-1 cells is listed in Table 1. SPGM-1 resembles a Pre-B cell line in the undifferentiated state. Upon IL-3 treatment, the phenotype changes to a more monocytic one, with Mac1 and F4/80 appearing and sIgM disappearing. The change in phenotype as ascertained using the Becton Dickenson FACSII flow cytometer (FACS), is mirrored in a change in morphology of SPGM-1 cells. Normal SPGM-1 cells appear as featureless round cells growing in suspension, slightly larger than lymphocytes. In cytospin samples, they resemble blast cells. After IL-3 differentiation, SPGM-1 cells become adherent and spread out on surfaces. In cytospin samples they show macrophage morphology (FIGS. 5 and 6).

In order to exclude any known cytokines as the bioactivity in the HSCL 197/17 CM, a series of available cytokines and less defined conditioned media were tested in the assay. The results are summarised in Table 2. Of these cytokines, only those human factors which also act on murine cells are of interest because, in the described bioassay, material from human origin (HSCL CM) is tested in a murine detection system. Keeping this in mind, only CM from HSCL, HUVEC and SPGM-1 itself have this activity. The only recombinant cytokine showing this activity is recombinant murine stem cell factor (SCF).

In addition to the direct testing of cytokines in the SPGM-1 bioassay, the cytokine profile of HSCL 197/17 was established using Northern Blot analysis and/or bioassays. Of the positive probes, only SCF is of potential interest, as M-CSF works as a differentiating cytokine on SPGM-1 (Table 3). The Northern Blot analysis suggests that HSCL 197/17 can produce SCF. Therefore, HSCL 197/17 CM was tested in three different assays for SCF bioactivity.

1. SCF has melanocyte differentiating properties. Embryonic neural crest cells were isolated and cultured in vitro in the presence of recombinant murine SCF plus the phorbolester PMA. In the presence of SCF, melanocyte differentiation is observed, whereas HSCL 197/17 CM has no activity on melanocyte differentiation.

2. SCF enhances colony size and yield in soft agar cultures of human colony-forming cells. Human colony-forming cells were purified as CD34+ lineage-cells and differentiated with a cocktail of factors in soft agar in the absence or presence of recombinant mouse or recombinant human SCF or HSCL 197/17 CM, respectively. SCF enhanced colony size and yield, whereas HSCL 197/17 CM had no effect on colony formation and size in this assay type.

3. If HSCL 197/17 CM contains SCF, it should be able to compete with [$^{125}$I] labelled SCF for the receptor binding sites on a detection cell. HSCL 197/17 CM was not able to displace recombinant rat [$^{125}$I] labelled SCF binding to P815 mastocytoma cells.

In all these assays, concentrations of HSCL 197/17 CM were used which elicit comparable proliferative responses to the respective SCF concentrations on SPGM-1 cells.

The results suggest that not enough bioactive SCF is produced and/or released by HSCL 197/17 to cause the effects in the SPGM-1 bioassay.

TABLE 1
Phenotype of SPGM-1

| Marker | specificity | untreated SPGM-1 cells | WEHI 3B CM treated SPGM-2 cells |
|---|---|---|---|
| Mac 1 (CD11b) | macrophage | − | + |
| Gr 1 | granulocyte | − | − |
| CD 3 | T lineage | − | − |
| CD 4 | T helper/monocytes | − | +? |
| CD 8 | T cytotox | − | − |
| TCR α β | T cells | − | − |
| Lyl (CD5) | T cells, some B cells | + | ++ |
| B220 (CD45R) | B cells | + | ++ |
| sIgM | pre B cells, B cells | + | + |
| κ L chain | B cells | − | − |
| λ L chain | B cells | − | − |
| G-5-2 | pre B cells, B cells | + | + |
| BP-1 | B cells | − | − |
| F4/80 | myeloid | W | + |
| Scal | Stem cells | − | − |
| Thy 1.2 | T cells | − | − |
| Mel 14 | lymphocytes | +(2p) | n.d. |
| ICAM 1 (CD54) | ubiquitous | + | n.d. |
| LFA 1 (CD11a) | lymphocytes | + | n.d. |
| Pgp (CD44) | lymphocytes wide | ++ | n.d. |
| HSA M1/69 | some lymphocytes | ++ | n.d. |
| MHC I | ubiquitors | − | − |
| MHC II | APC | − | − |

W = weak
2p = 2 populations

TABLE 2
Cytokine or conditioned media tested in SPGM-1 bioassay Effects of SPGM-1

| cytokine or CM medium | survival | proliferation | clonogenicity | differentiation | crosses species |
|---|---|---|---|---|---|
| rh IL-1α | − | | | | yes |
| rh IL-1β | − | | | | yes |
| rh IL-2 | − | | | | yes |
| rm IL-3 | + | + | − | Mθ, Gr | no |
| rh IL-7 | − | | | | yes |
| rh TNFα | − | | | | yes |
| b FGF | − | | | | yes |
| rm GM-SCF | + | +/− | − | Mθ, Gr | no |
| rm M-CSF | + | +/− | − | Mθ | yes |
| r G-CSF | + | +/− | − | Gr | yes |
| rh LIF | − | | | | yes |
| rm SCF | + | + | + | − | yes |
| rh PDGF AB | − | | | | yes |
| rh PDGF BB | − | | | | yes |
| h TGF β | − | | | | yes |
| α IFN | − | | | | yes |
| rh IFN γ | − | | | | no |
| rm IFN γ | anti-prolif | | | | no |
| ECGF | − | | | | yes |
| lo MW BGF | +/− | − | | | n.a. |
| PMA | − | | | | yes |
| LPS | − | | | | yes* |
| HSCL 197/17CM | + | + | + | | n.a. |
| HUVEC CM | + | + | + | − | n.a. |
| SPGM1 CM | + | + | + | − | n.a. |

| Abbrev: | HUVEC CM | human umbilical vein endothelial cell conditioned medium |
|---|---|---|
| | PRP | platelet rich plasma |
| | HSCL CM | human stroma cell line conditioned medium |
| | SPGM1 CM | suspension PGM1 cell line conditioned medium |
| | n.a. | not applicable as mixture |
| | LPS | bacterial lipopolys archoride (not active in C3H/HeJ mice) |
| | PMA | phorbal myristate acetate |
| | Mθ | macrophage |
| | Gr | granulocytes |

TABLE 3
Characterisation of cytokine profile of the human stromal cell line 197/17

| Cytokine | (1) Northern blot analysis | (2) Bioactivity | (3) crosses species |
|---|---|---|---|
| IL-1 α | neg. | neg. | + yes |
| IL-3 | neg. | n.d. | − no |
| IL-4 | neg. | n.d. | − no |
| IL-7 | neg. | n.d. | + yes |
| G-CSF | neg. | neg. | + yes |
| GM-CSF | neg. | neg. | − no |
| M-CSF | pos. | n.d. | + yes |
| IL-6 | pos. | n.d. | + yes |
| SCF | pos. (PCR) | not detectable | + yes |

1) cellular mRNA was isolated using standard procedures. RNA was transferred to membranes and hybridized with the respective radiolabeled probes.
2) bioactivity was tested in bioassays. SCF bioactivity was ascertained in melanocyte differentiation assay, colony enhancing activity of human colony forming cells, and in receptor binding competition assay on a mouse detection cell.
3) only cross species acting cytokines could be responsible for bioactivity of human HSCL CM on mouse SPGM-1 cells.

EXAMPLE 3

Purification of the Novel Cytokine

1. Preparation of Human Stromal Cell Conditioned Medium (HSCL 197/17 CM)

The SV40 large T transfected human bone marrow stromal cell line HSCL 197/17 was maintained in 175 cm² tissue culture flasks containing RPMI 1640/IMDM culture medium (1:1 (v/v)) in the presence of 5% (v/v) foetal calf serum (FCS) batch #445 at 37° C./5% $CO_2$ in air. Upon reaching confluency, cells were removed with trypsin/EDTA and seeded into 800 cm² roller bottles containing 500 ml RPMI 1640/IMDM medium 2% (v/v) FCS. Once the cells were confluent conditioned medium was collected every 72 hrs, and the cells re-fed. The conditioned medium was stored either at 4° C. in the presence of sodium azide 0.02% (w/v) or frozen at −20° C.

2. Anion-exchange Chromatography (FIG. 7)

A ten liter batch of HSCL 197/17 CM was concentrated 10–20 times using a Sartorius Mini Crossflow concentrator (Sartorius) fitted with a cellulose triacetate filter with a molecular weight cut-off of 20,000, and exchanged into 10 mM TRIS-HCl buffer pH 8.0, containing 0.02% (v/v) Tween-20/0.02% (w/v) sodim azide. The concentrate was applied to a 2.6×39 cm column of DEAE-sepharose CL-6B (Pharmacia) equilibrated in the same buffer, and the column eluted isocratically with 200 ml equilibration bier. Bound proteins were eluted with successive linear gradients of 0–1.0M NaCl (500 ml) and 1–2.0M NaCl (100 ml). Five milliliter fractions were collected at a flow rate of 0.5 ml/min and were assayed for PGM-1 activity at a dilution of 1:50 and 1:125.

3. Gel Filtration Chromatography (FIG. 8)

Fractions that eluted from the anion exchange matrix in the breakthrough, and containing PGM-1 activity were pooled, concentrated using an amicon stirred cell concentrator fitted with a YM-10 membrane (Amicon). The concentrated sample was applied to a 96×2.6 cm column of ACA 44 (LKB) equilibrated in mouse tonicity phosphate buffered saline pH 7.2 containing 0.02% (v/v) Tween-20/0.02% (w/v) sodium azide, and was eluted isocratically at a flow rate of 0.5 ml/min. Aliquots of 5 ml fractions were collected and assayed for PGM-1 activity at a dilution of 1:100 and 1:500.

4. Hydrophobic Interaction Chromatography (FIG. 9)

Fractions that eluted from the gel filtration column between 40 KDa and 20 KDa and contained the PGM-1 activity were pooled, concentrated and exchanged into 100 mM sodium phosphate buffer pH 7.0 containing 1.0M sodium sulphate, 0.02% (v/v) Tween-20 and 0.02% (w/v) sodium azide. Half the sample was applied to a 3.5×1.0 cm column of phenyl-sepharose CL-4B (Pharmacia) equilibrated in the same buffer. After a 5 ml wash in equilibrating buffer, bound proteins were eluted with successive gradients of 0–10% (w/v) ethylene glycol in 100 mM sodium phosphate buffer pH 7.0 (15 ml) and 10–50% (w/v) ethylene glycol in the same buffer (10 ml). Aliquots of 1 ml fractions were collected at a flow rate of 0.5 ml/min and were assayed at a dilution of 1:50 and 1:500 for PGM-1 activity.

5. Reverse Phase High Performance Liquid Chromatography (FIG. 10)

RP-HPLC was carried out using a Hewlett Packard 1090 system fitted with a diode array detector and a 6 mm flow cell. Fractions that bound to phenylsepharose CL-4B or eluted from ACA 44 between 40 and 20 KDa and contained PGM-1 activity were pooled and applied to a Aquapore RP300 C8 7×250 mm, 7 um particle size column (Applied Biosystems) equilibrated in water containing 0.1% trifluroacetic acid (TFA). After a 20 ml wash in the equilibrating buffer, elution was carried out with a linear gradient from 0–60% (v/v) acetonitrile containing 0.085% (v/v) TEA (60 ml). 1 ml fractions were collected at a flow rate of 1 ml/min into 50 ul 1M ammonium bicarbonate containing Tween-20 (final concentration of 0.02%). Fractions were assayed for PGM-1 activity at a dilution of 1:50 to 1:500.

6. Preparative SDS-PAGE (FIG. 11)

Fractions containing PGM-1 activity that eluted from RP-HPLC were electrophoresed on a 15% (w/v) polyacrylamide gel with a 4% (w/v) acrylamide stacking gel (0.75 mm thick) in the presence of SDS under non-reducing conditions. The track from which protein was to be recovered was separated from the remainder of the gel and sliced into 1 mm strips which were then homogenised in 6M guanidine-HCl containing 1 mg/ml bovine serum albumin (carrier protein) using a teflon plunger fired to an electric drill. The homogenate was left overnight at 4° C., and exchnaged into IMDM/1% (v/v) FCS (#445) using NAP-5 gel filtration columns (Pharmacia). Each fraction was assayed for PGM-1 activity.

7. Preparation of Samples for Bioassay

Fractions from chromatography were exchanged into IMDM containing 1% (v/v) FCS (#445) using pre-packed columns of Sephadex G25 (NAP-5 columns; Pharmacia) according to the manufacturers instructions. The exchanged fractions were then sterilised by passage through 0.45 um filters (Dynagard).

8. Results of Purification

The detectable novel cytokine from HSCL 197/17 CM does not appear to bind to DEAE-Sepharose CL-6B (FIG. 7) under conditions of low ionic strength and high pH (10 mM TRIS-HCl pH 8.0) suggesting that the activity is basic in nature and has an isoelectric point (pI) greater than 8. This step provides an ideal separation of the detectable biological activity from other proteins present in the conditioned medium, with up to 98% of the proteins binding to DEAE-sepharose CL-6B.

The biological activity elated from a gel filtration column (ACA 44) in the 40–20 KDa region (FIG. 8) under physiological non-denaturing conditions. This step separates the biological activity from approximately 95% of the remaining protein.

Active fractions from the gel filtration step were further separated by hydrophobic interaction chromatography on a phenyl-sepharose CL-4B column (FIG. 9) followed by passage through a C8 reverse phase HPLC column (FIG. 10). The PGM-1 activity eluted at an acetonitrile concentration of 45%. The activity was not denatured by acetonitrile or low pH from the TFA.

FIG. 11 shows an SDS-PAGE gel of purified protein of HSCL 197/17 CM purified as above. In relation to FIG. 11, PGM-1 activity semi-puified from HSCL 197/17 CM using anion exchange chromatography, gel filtration, hydrophobic interaction chromatography, and RP-HPLC, was electrophoresed on a 15% polyacrylamide gel in the presence of SD5 under non-reducing conditions. Lanes 2–8 represent fractions 72–78 from the RP-HPLC in which PGM-1 activity was detected in fractions 75 and 76 (lanes 5 and 6). Molecular weight markers are shown in lane 1, and were phosphorylase B (97.4 KDa), bovine serum albumin (66 KDa), ovalbumin (43 KDa), and carbonic anhydrase (31 KDa). The starting material that went onto the column is shown in lane 9.

PGM-1 activity could be recovered from SDS PAGE under non-reducing conditions, and the activity migrated with an apparent molecular weight of between 43–33 KDa (FIG. 12).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

We claim:

1. The SPGM-1 cell line deposited at Public Health Laboratory Service, European Collection of Animal Cell Cultures, Porton Down, Salisbury, on 26 Apr., 1991 under Accession No. 91042620.

* * * * *